(12) United States Patent
Sessoms et al.

(10) Patent No.: US 10,636,002 B2
(45) Date of Patent: Apr. 28, 2020

(54) METHODS AND APPARATUS FOR INTERACTIVE WORKFLOW FOR PATIENT SCHEDULING

(71) Applicant: ScheduleWise, LLC, Phoenix, AZ (US)

(72) Inventors: Mark N. Sessoms, Sandy Springs, GA (US); Gary E. Hamilton, Gilbert, AZ (US)

(73) Assignee: Schedulewise, LLC, Phoenix, AZ (US)

( * ) Notice: Subject to any disclaimer, the term of this patent is extended or adjusted under 35 U.S.C. 154(b) by 979 days.

(21) Appl. No.: 14/831,559

(22) Filed: Aug. 20, 2015

(65) Prior Publication Data

US 2016/0055445 A1 Feb. 25, 2016

Related U.S. Application Data

(60) Provisional application No. 62/039,698, filed on Aug. 20, 2014.

(51) Int. Cl.
*G06Q 10/06* (2012.01)
*G06Q 50/22* (2018.01)

(52) U.S. Cl.
CPC ..... *G06Q 10/063114* (2013.01); *G06Q 50/22* (2013.01)

(58) Field of Classification Search
CPC .............. G06Q 50/22; G06Q 10/06
USPC ........................................................ 705/2
See application file for complete search history.

(56) References Cited

U.S. PATENT DOCUMENTS

| | | | | |
|---|---|---|---|---|
| 5,129,057 A | * | 7/1992 | Strope | G06F 15/0266 345/629 |
| 5,659,768 A | * | 8/1997 | Forbes | G06Q 10/06 704/1 |
| 5,692,125 A | * | 11/1997 | Schloss | G06Q 10/06 705/7.16 |
| 2004/0039628 A1 | * | 2/2004 | Thompson | G06Q 10/0631 705/2 |
| 2007/0245300 A1 | * | 10/2007 | Chan | G06Q 10/06 717/105 |

* cited by examiner

*Primary Examiner* — Trang T Nguyen
(74) *Attorney, Agent, or Firm* — The Noblitt Group, PLLC

(57) ABSTRACT

Methods and apparatus for interactive workflow for patient scheduling according to various aspects of the present technology may comprise a schedule module configured to retrieve a workflow schedule and a visualization module configured to convert the retrieved schedule into a diagram comprising a plurality of patient block elements corresponding to a plurality of individual patient schedules and arranged according to a workflow schedule wherein each individual patient schedule in the diagram may comprise a first patient block element corresponding to the time for a start task and a second patient block element corresponding to the time for an end task. The visualization module may be further configured to allow a user to adjust the workflow schedule by selectively moving either the first or the second patient block element.

18 Claims, 6 Drawing Sheets

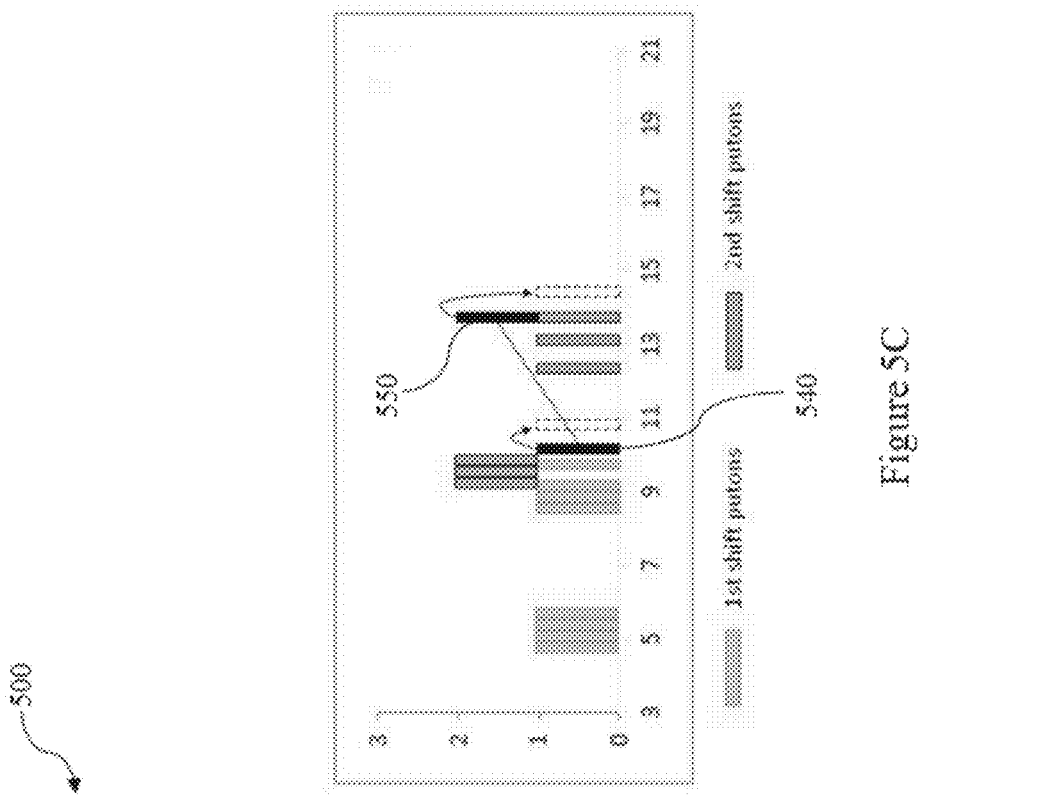
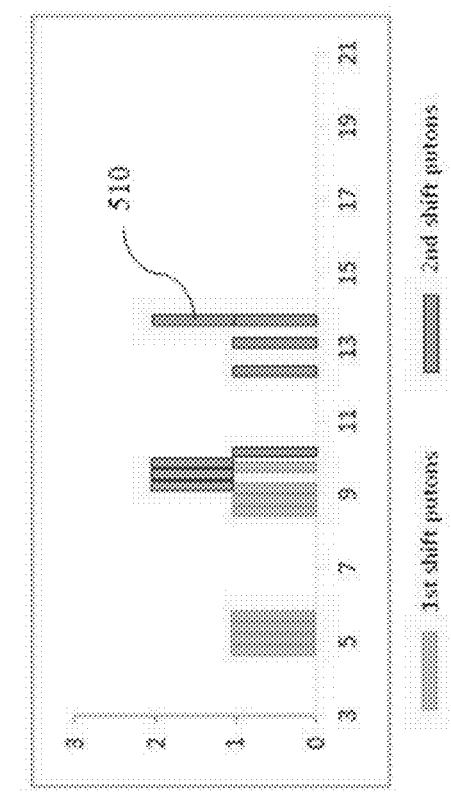
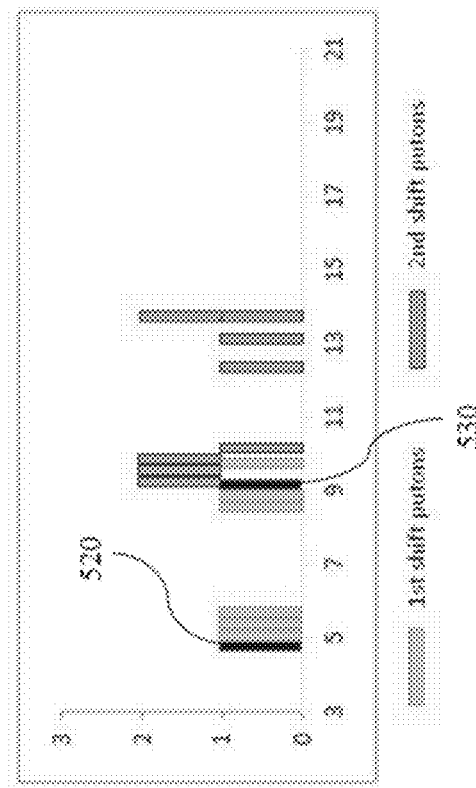
Figure 5A
Figure 5B
Figure 5C

METHODS AND APPARATUS FOR INTERACTIVE WORKFLOW FOR PATIENT SCHEDULING

CROSS-REFERENCES TO RELATED APPLICATIONS

This application claims the benefit of U.S. Provisional Patent Application No. 62/039,698, filed Aug. 20, 2014, and incorporates the disclosure of the application by reference.

BACKGROUND OF INVENTION

Currently available methods and products for creating a workflow schedule do not provide sufficient levels of information to determine inefficiencies or the use of excessive resources in the workflow schedule. A few currently available methods and products fail to provide a visualized representation of the workflow. Microsoft Excel®, for example, remains the tool of choice for creating patient schedules. However, a key drawback to Excel® is the lack of a visualized schedule which may result in any workflow related issues to impact the entirety of the schedule. Furthermore, Excel® is incapable of providing an interactive workflow schedule as disclosed in the present technology.

A workflow line chart may be implemented to better visualize the workflow. A typical workflow line chart may display the number of activities/tasks on a vertical axis and the duration it takes to perform those activities/tasks on a horizontal axis. In this manner, it is easy to visualize workflow issues because one can more easily see when two activities/tasks are scheduled for the same timeframe. Yet a key drawback to the workflow line chart is the difficulty in determining the source/cause of the workflow issue. In other words, in the context of a dialysis treatment center, it is difficult to determine which patient events are contributing to the workflow issues. Furthermore, currently available workflow line charts are limited in their interactive capabilities and often do not provide the user with sufficient capability to edit the workflow schedule.

In the context of a dialysis center, one problem to be solved is not the visualization of the availability of resources or the assignment of resources; instead, the aim is to visualize the workflow of the patient care staff in relation to the patients' scheduled treatments. Other currently available visualized workflow representations such as Gantt charts also fail to adequately indicate where workflow issues may arise. The Gantt chart fails to provide a quick visual method for the user to identify workflow issues, leading these workflow issues to be easily overlooked. Furthermore, a Gantt chart may not provide interactive capabilities to edit the workflow schedule.

SUMMARY OF THE INVENTION

Methods and apparatus for interactive workflow for patient scheduling according to various aspects of the present technology may comprise a schedule module configured to retrieve a workflow schedule and a visualization module configured to convert the retrieved schedule into a diagram comprising a plurality of patient block elements corresponding to a plurality of individual patient schedules and arranged according to a workflow schedule wherein each individual patient schedule in the diagram may comprise a first patient block element corresponding to the time for a start task and a second patient block element corresponding to the time for an end task. The visualization module may be further configured to allow a user to adjust the workflow schedule by selectively moving either the first or the second patient block element.

BRIEF DESCRIPTION OF THE DRAWING FIGURES

A more complete understanding of the present technology may be derived by referring to the detailed description and claims when considered in connection with the following illustrative figures. In the following figures, like reference numbers refer to similar elements and steps throughout the figures.

Figure 3A:
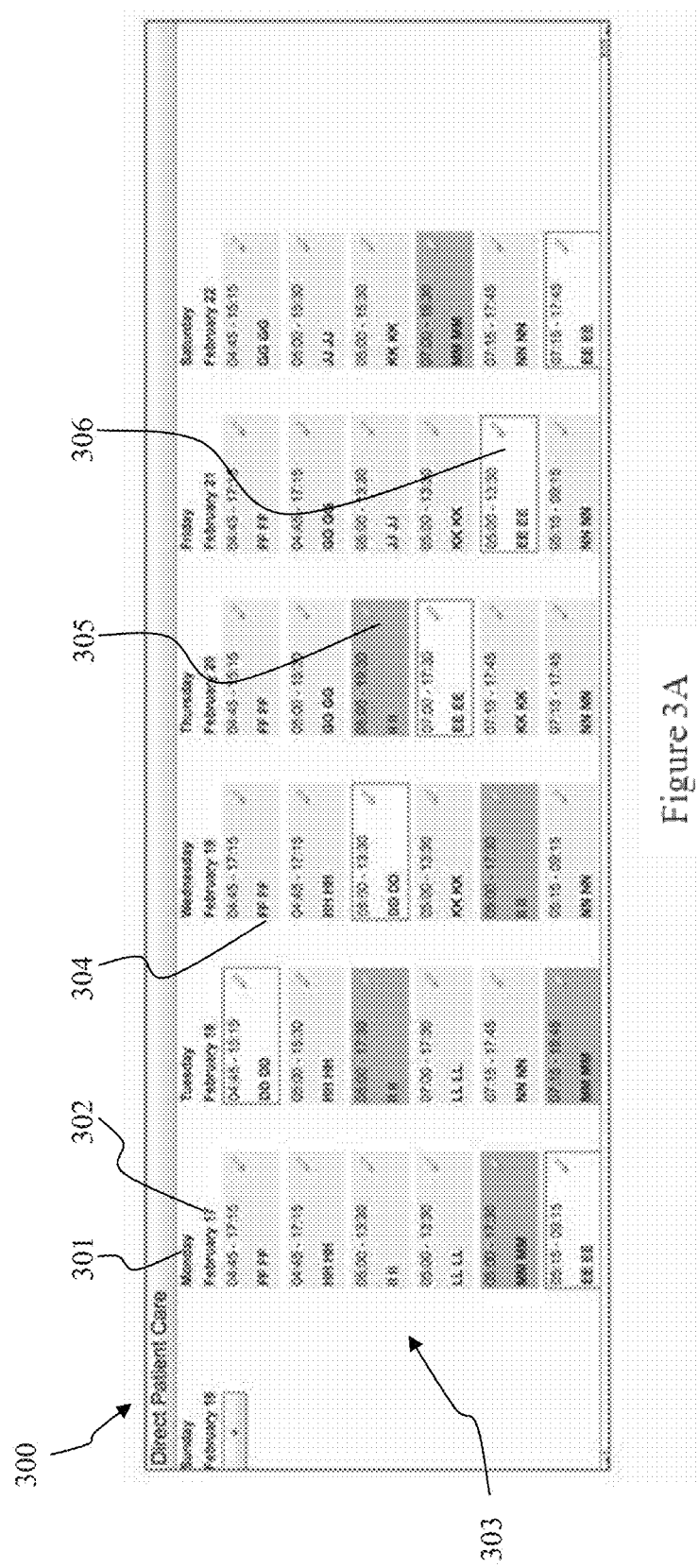
Figures 3B, 3C:
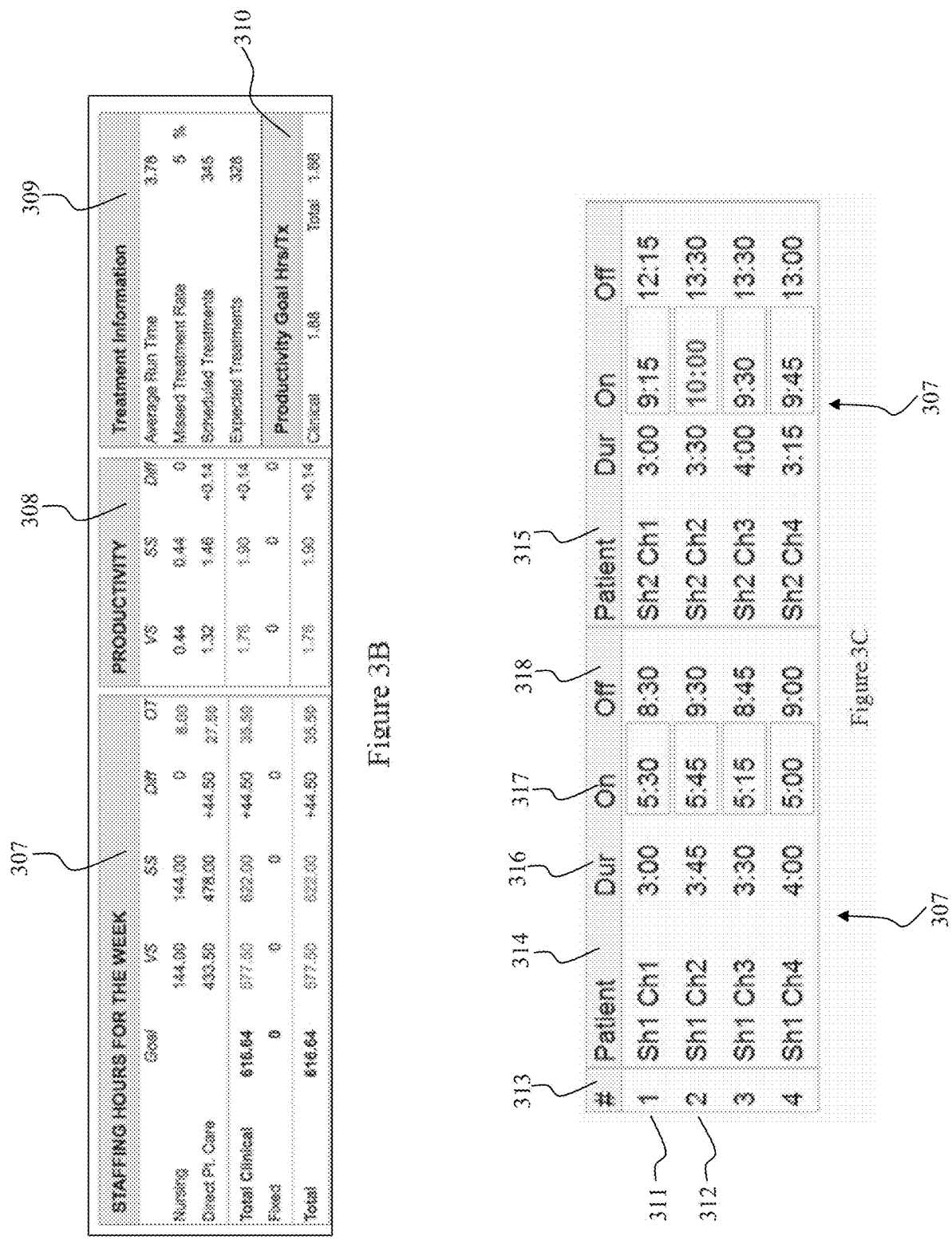
Figure 4:
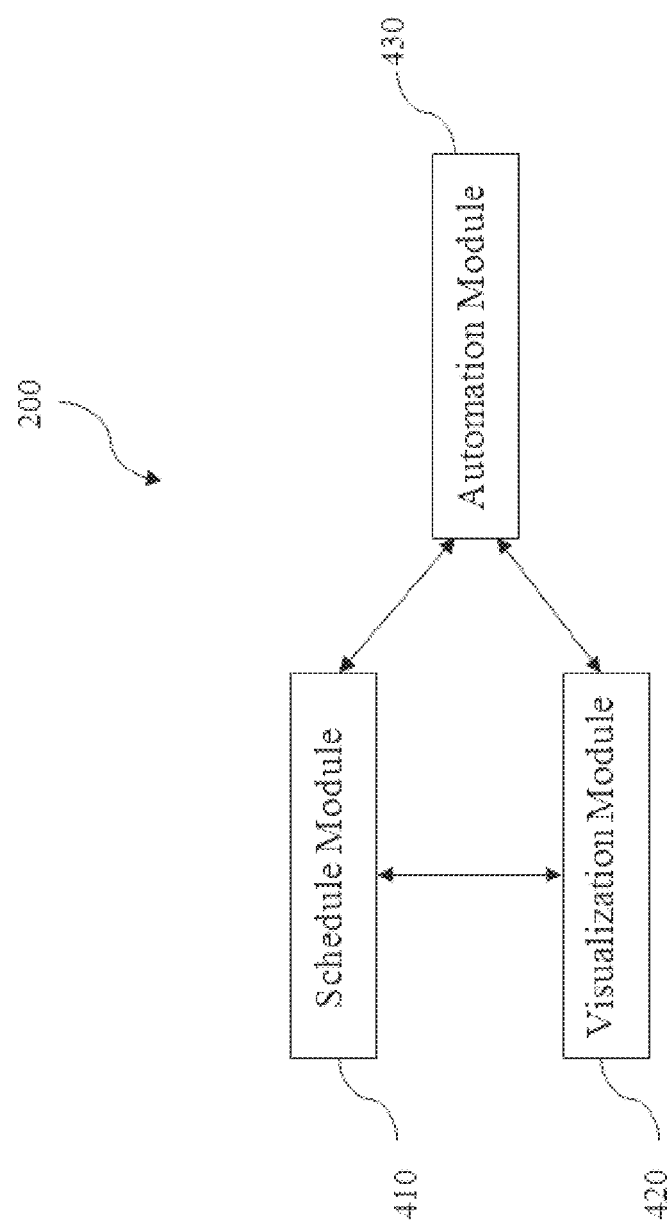

FIG. 3A-C representatively illustrate a first, second, and third exemplary output of a schedule module;

FIG. 4 is a block diagram representatively illustrating the schedule, visualization, and automation modules used by the interactive workflow scheduling system; and FIG. 5A-C representatively illustrate a connected blocks diagram.

Elements and steps in the figures are illustrated for simplicity and clarity and have not necessarily been rendered according to any particular sequence. For example, steps that may be performed concurrently or in different order are illustrated in the figures to help to improve understanding of embodiments of the present technology.

DETAILED DESCRIPTION OF EXEMPLARY EMBODIMENTS

The present technology may be described in terms of functional block components and various processing steps. Such functional blocks may be realized by any number of hardware or software components configured to perform the specified functions and achieve the various results. For example, the present technology may employ systems, technologies, devices, algorithms, designs, services, and the like, which may carry out a variety of functions. In addition, the present technology may be practiced in conjunction with any number of hardware and software applications and environments. For example, the present technology may be practiced in conjunction with any number of patient care facilities, patient scheduling systems, workforce scheduling and/or allocation systems, websites, software applications, and computing devices such as servers, computer databases, personal computers, and portable computing devices, and the system described is merely one exemplary application for the invention.

Methods and apparatus for interactive workflow for patient scheduling according to various aspects of the present technology may operate in conjunction with any suitable computing process or device, interactive system, input system or method, output system or method, and/or telecommunication network. Various representative implementations of the present technology may be applied to any computing device or application configured to communicate via a telecommunication network. Certain representative implementations may comprise, for example, program code stored on any combination of computing devices, wherein the program code facilitates inputting, outputting, visualizing, and/or improving, automating, and/or optimizing patient scheduling. Various representative algorithms may be implemented with any combination of data structures, objects, processes, routines, other programming elements, and computing components and/or devices.

The present technology may involve multiple programs, functions, computing devices (such as client computers and/or servers), and the like. While the exemplary embodiments are described in conjunction with conventional computing devices, the various elements and processes may be implemented in hardware, software, or any combination of hardware, software, and other systems. Further, the present technology may employ any number of conventional techniques for generating and/or presenting content (such as a patient and/or workforce schedule), interfacing a computing device to a network, transmitting and/or receiving data, providing a user interface, communicating information, interfacing with a user, detecting and/or analyzing input to a computing device, gathering data, collecting patient-specific information, tracking patients and technicians, tracking statistics relating to patient care, adjusting patient schedules, collecting and managing user accounts and information, calculating statistics, generating reports, and the like.

A computing device may comprise conventional components, such as a processor, a local memory such as RAM, long term memory such as a hard disk, solid-state drive, or electronic non-volatile computer storage medium, a network adaptor, and any number of input and/or output devices such as a keyboard, mouse, monitor, touch screen, microphone, speaker, motion sensor, orientation sensor, light sensor, and the like. The various memories of the computing device may facilitate the storage of one or more computer instructions, such as a software routine and/or software program, which may be executable by the processor to perform one or more methods, processes, and/or steps of the disclosed technology. The computing device may comprise any suitable device or system such as: a personal computer, server, mobile phone, smart phone, tablet computer, kiosk, portable computer, and the like.

Further, databases, systems, and/or components of the present technology may comprise any combination of databases, systems, and/or components at a single location or at multiple locations. Each database, system, and/or component of the present technology may comprise any suitable security features, such as one or more firewalls, access codes, encryption, de-encryption, compression, decompression, and/or the like. Systems and methods according to the present technology may comprise one or more databases configured to store data according to the present technology. In some embodiments, data may be shared and/or linked among the various databases. The one or more databases may be implemented using database schemes such as IBM DB2, Oracle, MySQL, and/or Microsoft SQL Server, or any other database scheme, whether now known or later developed. Transferring data to and from the one or more databases may be accomplished using a communicative coupling, for example a network connection to the Internet or a local area network (LAN).

The present technology may be embodied as a method, a system, a device, and/or a computer program product. Accordingly, the present technology may take the form of an entirely software embodiment, an entirely hardware embodiment, or an embodiment combining aspects of both software and hardware. Furthermore, the present technology may take the form of a set of instructions, such as a computer program product, for causing a processor and/or computing device to perform a desired function, stored on a non-transitory computer-readable storage medium having computer-readable program code embodied in the storage medium. Any suitable computer-readable storage medium may be utilized, including, but not limited to, hard disk drive, CD-ROM, optical storage devices, magnetic storage devices, USB memory devices, any appropriate volatile or non-volatile memory system, and the like or any combination thereof. The present technology may take the form of a downloadable and/or cloud-based non-downloadable computer program product and/or methods.

Software and/or software elements according to various aspects of the present technology may be implemented with any programming, scripting, or computer language or standard, such as, for example, AJAX, C, C++, Java, JavaScript, COBOL, assembly, PERL, extensible Markup Language (XML), PHP, CSS, HL7, GNU Mathematical Programming Language (GMPL), etc., or any other programming and/or scripting language, whether now known or later developed. Further, the present technology may be used in conjunction with a computing device running any operating system such as any version of Windows, MacOS, OS/2, BeOS, Linux, UNIX, Android, iOS, or any other operating system, whether now known or later developed, and the present technology may be used in conjunction with any software application operating on such a computing device.

In addition, the present technology may employ any number of conventional techniques for data transmission, signaling, data processing, network control, and the like. Computing devices according to various aspects of the present technology may communicate with each other by one or more telecommunication networks. The telecommunication network may comprise a collection of terminal nodes, links, and any intermediate nodes which are connected to enable communication (including transfer of data) at a distance between the terminal nodes. In some embodiments, a terminal node may comprise a computing device. The telecommunication network may comprise any suitable communication system, such as the Internet, an intranet, an extranet, WAN, LAN, satellite communications, cellular radio network, wireless network, telephone network, cable network, and the like. Moreover, computing devices according to various aspects of the present technology may communicate over the telecommunication network using TCP/IP, HTTP, HTTPS, FTP, IPX, AppleTalk, IP-6, NetBIOS, OSI, and/or any number of existing or future protocols. The telecommunication network may be simply referred to as a network.

Methods and apparatus for interactive workflow for patient scheduling according to various aspects of the present technology may retrieve and/or store a schedule (comprising either one of or both a patient appointment schedule and a staff workflow schedule), present the schedule, receive user input corresponding to the schedule (such as queries about and/or alterations to the patient schedule), and adjust the presentation of the schedule accordingly. The schedule may comprise a patient schedule, appointment schedule, workflow schedule, treatment schedule, staff hour schedule, and the like. Methods and apparatus for interactive workflow for patient scheduling system may visually present the schedule using a diagram, such as a "Connected Blocks" diagram (described below). Methods and apparatus for interactive workflow for patient scheduling system may also be suitably configured to automate creation, improvement, and/or optimization of the schedule.

Methods and apparatus for interactive workflow for patient scheduling according to various aspects of the present technology may be applied to any facility, program, or activity that utilizes a schedule. For example, the present technology may be applied to a dialysis treatment center, oncology center, outpatient care facilities, dentistry, and the like.

Figure 1:
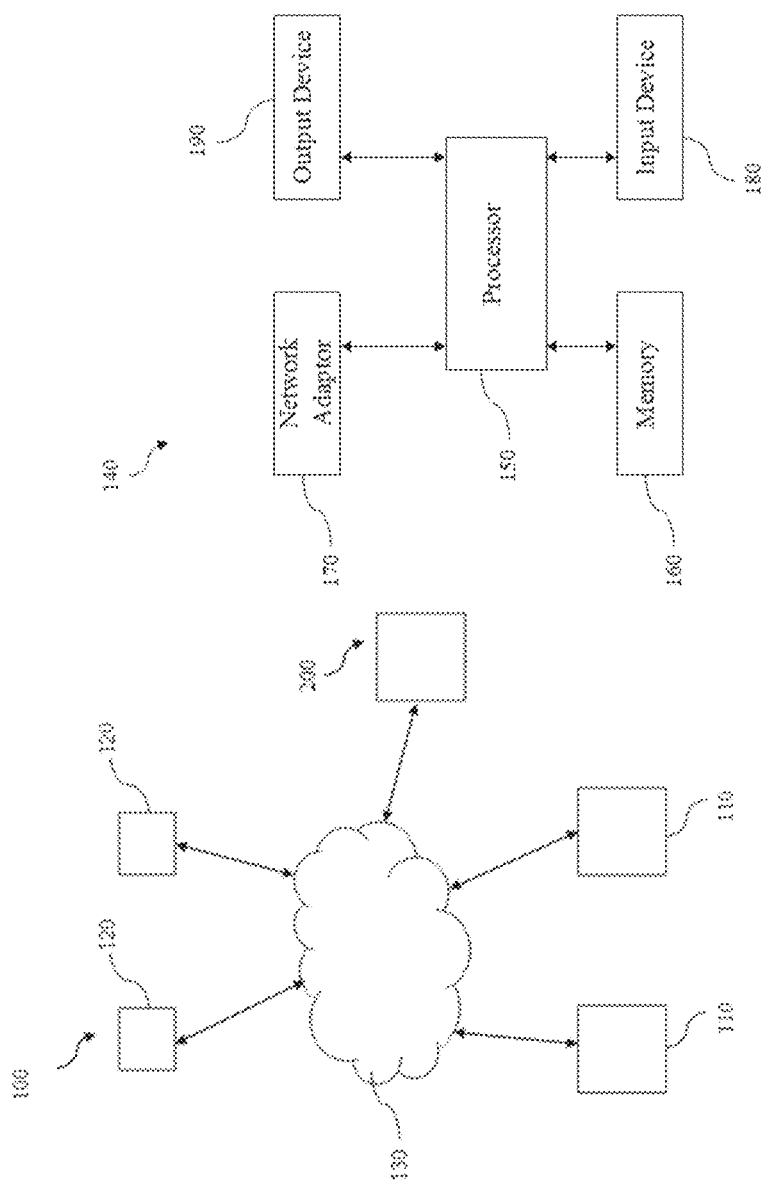
FIG. 1A is a block diagram representatively illustrating a scheduling system.
FIG. 1B is a block diagram representatively illustrating a computing device capable of operating an embodiment of the present technology.

Referring now to FIG. 1A, a scheduling system 100 implementing or otherwise operating the interactive workflow scheduling system 200 may comprise one or more computing devices. The one or more computing devices may be configured to exchange data to facilitate changing the information presented by one or more of the computing devices. For example, in one embodiment, the scheduling system 100 may comprise one or more client devices 110 and one or more servers 120 communicatively coupled to each other via one or more networks 130, which may be collectively configured to facilitate changing the information presented to a user of the client device 110.

In one embodiment, the client device 110 and one or more servers 120 may be combined into a single device. In some embodiments, multiple servers 120 may be combined into a single device to form a single server. As used herein, a computer system according to the present technology may comprise one or more client devices 110 and/or one or more servers 120.

The client device 110 and the one or more servers 120 may comprise any suitable computing device, for example a special-purpose computer, a general-purpose computer specifically programmed and/or otherwise configured/adapted to implement or otherwise execute (whether alone or in combination with other one or more other computing devices) the systems and methods of the present technology, for example the methods and apparatus for interactive workflow scheduling system 200, and the like. Such a computing device may comprise a personal computer, server, mobile phone, smart phone, wearable computer, tablet computer, television, kiosk, and the like.

Referring now to FIG. 1B, a computing device 140 may comprise conventional components, such as any number of processors 150 communicatively coupled with any number of memory devices 160, any number of network adaptors 170, and any number of input 180 and/or output 190 devices such as a keyboard, mouse, monitor, touch-sensitive input device such as touch screen, touch sensor, and the like, microphone, speaker, motion sensor, orientation sensor, light sensor, and the like. A server 120 need not comprise an input device 180 and/or output device 190. The memory device 160 may comprise any combination of local memory such as RAM, long term memory such as a hard disk drive, and the like. The processor 150 may be configured to access (read and/or write) the memory device 160.

The memory device 160 may facilitate the storage of data and/or one or more computer instructions, such as a software routine and/or software program, which may be executable by the processor 150 to perform the methods of the present technology. The processor 150 may be configured to provide the output device 190 with content to present and may be configured to receive input from the input device 190. In an embodiment, the input device 180 may be integrated with the output device 190, such as in a touch screen display. In an embodiment, the computing device 140 may comprise a network adaptor 170 that allows the processor 150 to communicate with another computing device 140. For example, the network adaptor 170 may comprise an Ethernet adaptor, a wireless networking adaptor, a radio networking adaptor, a USB networking adaptor, and the like.

Figure 2:
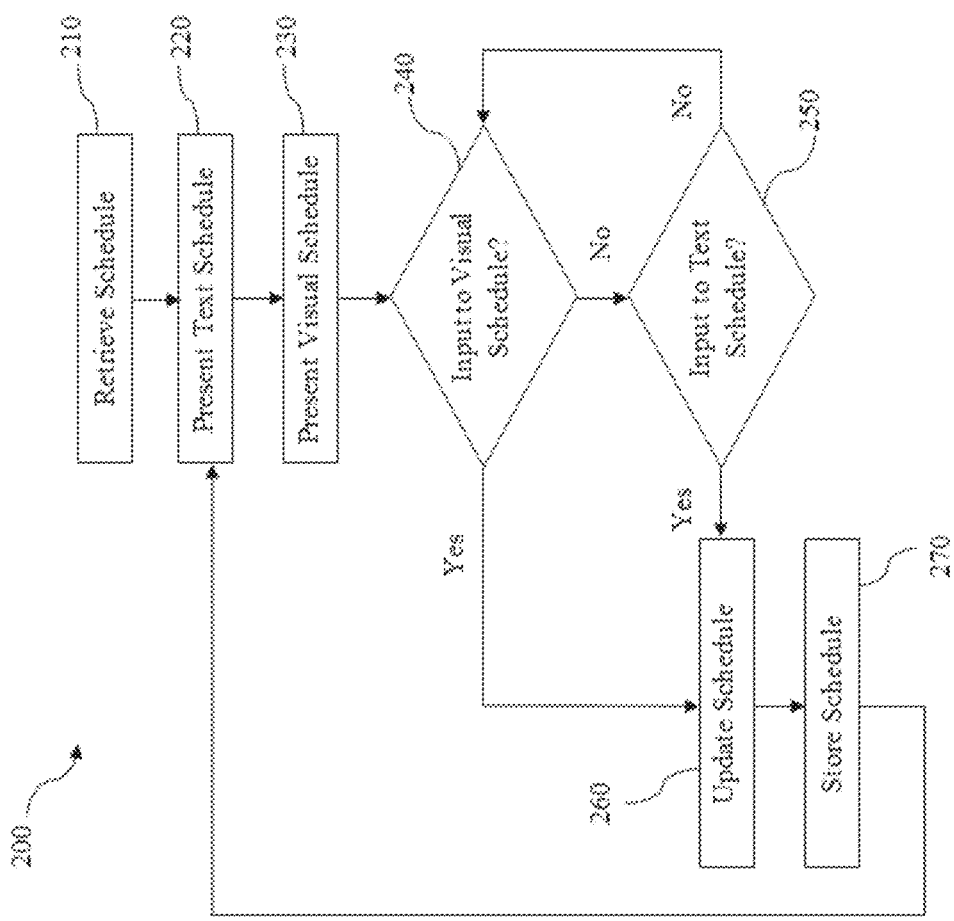
FIG. 2 is a flow chart representatively illustrating an interactive workflow scheduling system.

Referring to FIG. 2, in one embodiment, the interactive workflow scheduling system 200 may comprise retrieving a schedule from a memory (210), presenting the retrieved schedule in a text-based format (220), and presenting the retrieved schedule in a visual format (230). The interactive workflow scheduling system 200 may be configured to be communicatively coupled to the network 130 such that information may be transmitted and/or received between the interactive workflow scheduling system 200 and the scheduling system 100.

Referring now to FIG. 3A-C, in one embodiment, a text-based schedule 300 may comprise any suitable presentation of the schedule using text as the primary method to convey the schedule information. For example, the text-based schedule 300 may indicate a day of the week 301, a calendar date 302, activities currently scheduled for that date broken down by a series of time blocks 303, and/or a staff person currently assigned to perform a set of tasks 304 within a given time block. The text-based schedule 300 may utilize various color schemes and/or borders to aid in presenting the text based schedule. For example, having alternating (or different) colored boxes 305, 306 may create a more visually appealing schedule than one where all the rows are of the same color.

Referring now to FIG. 3B, in one embodiment, the text-based schedule 300 may include additional functionality configured to provide a user viewing the schedule with advanced information, statistics, and/or metrics related to either one of a patient, the staff member, availability of equipment, and the like. For example, one of the additional functionalities may be providing the user with information about the amount of hours each staff has worked for a time period 307. Another functionality of the text-based schedule may be to display productivity information 308. Furthermore, the text-based schedule may be configured to display information regarding treatment information 309, such as average run time, a rate of missed treatments, a number of treatments scheduled, an expected number of treatments for a given period, and the like. Yet another functionality may be to present the user with information relating to a set of goals 310 related to a specific location/center, such as productivity goals.

In one embodiment, the text-based schedule 300 may be configured to selectively display information based on user selected and/or activated preference(s). For example, referring now to FIG. 3C, the text-based schedule 300 may provide a basic or otherwise high level view of that day's schedule. For example, one column may be configured to display information regarding the number of available chairs 311, 312 in a dialysis center 313. A second column may be configured to display information about a specific patient 314, 315 scheduled to occupy any of the number of available chairs 311, 312. A third column may be configured to display the duration 316 (i.e., treatment duration time) for each specific patient (e.g., a 3-hour duration). A fourth column and fifth column may be configured to display tasks associated with a specific patient's treatment such as a start (on) 317 and an end (off) 318 time that corresponds to the treatment duration 316. These five columns may be grouped together to create a first shift schedule 319. A second group of the same five columns may be grouped together to create a second shift schedule 320 and so forth.

Referring again to FIG. 2, the interactive workflow scheduling system 200 may further comprise checking for user input to the text-based schedule (250), and updating (260) and storing (270) the schedule to the memory if user input was received. After the schedule has been updated (260), the presentation of the text-based schedule (220) and/or the presentation of the visualized schedule (230) to the user (or user device) may be refreshed or otherwise updated to reflect the most current version of the schedule.

Input to the text-based schedule (250) may be performed manually. For example, a user may manually input information related to a patient such as their personal information and medical information. Input to the text-based schedule (250) may also be performed automatically. For example, the interactive workflow scheduling system 200 may be configured to automatically update the text-based schedule in a predetermined time interval (e.g., daily, weekly, bi-weekly, and the like) according to any suitable criteria such as pre-scheduled and/or recurring appointments.

In some embodiments, a combination of manual and automatic inputs may be utilized. For example, the user may manually input information that affects a batch (i.e., more than one) of items in the text-based schedule, and the interactive workflow scheduling system 200 may be configured to apply the same effect to any other related matters in the text-based schedule. For instance, it may be the case that a patient requires their next appointment to be moved ahead or back by an amount of time. By moving one appointment, future appointments may also need to be modified. Thus, the interactive workflow scheduling system 200 may be configured to receive the manual input to adjust the one specific appointment and then automatically applying the same effect (e.g., moving one appointment forward by one week) for all (or any other number) of future appointments.

The interactive workflow scheduling system 200 may further comprise checking for user input to the visualized schedule (240), and updating (260) and storing (270) the schedule if user input was received. For example, a patient may need to reschedule and/or cancel one of their appointments which may leave an open spot for a different patient. Alternatively, a patient may relocate to another dialysis center, which may free up that patient's time block in the time-based schedule for the remainder of their treatment cycle. For example, if a patient is scheduled for 3 months of treatment and moves to a different state 1 month into their treatment, the remaining 2 months may be opened up for a different patient to use. In these situations, the dialysis center may need to adjust the schedule to maximize the number of available treatment chairs.

As discussed in more detail below, input to the visualized schedule (240) may be performed manually. For example, a user may manually input and/or move information related to a patient such as their appointment time. Input to the visualized schedule (240) may also be performed automatically. For example, the interactive workflow scheduling system 200 may be configured to automatically update the visualized-based schedule in a predetermined time interval (e.g., daily, weekly, bi-weekly, and the like).

In one embodiment, inputs to the text-based schedule (250) (for example, an appointment change) may automatically be reflected in the visualized schedule. Likewise, inputs to the visualized schedule (240) may automatically be reflected in the text-based schedule. For example, if a staff member manually adjusts a patient's appointments forward by 1 week using the text-based schedule, the interactive workflow scheduling system 200 may be configured to save the new inputs and update (260) one of, or both, the text-based schedule as well as the visualized schedule based on the received inputs to the text-based schedule. Similarly, if a staff member manually adjusts a patient's appointment forward by 1 week using the visualized schedule, the interactive workflow scheduling system 200 may be configured to save the new inputs and update (260) one of, or both, the visualized schedule as well as the text-based schedule based on the received inputs to the visualized schedule.

Referring now to FIG. 4, the interactive workflow scheduling system 200 may comprise a schedule module 410, a visualization module 420, and an automation module 430. In an embodiment, the schedule module 410 and visualization module 420 may operate without the automation module 430. In an embodiment, the schedule module 410 and automation module 430 may operate without the visualization module 420. In an embodiment, the visualization module 420 and the automation module 430 may operate without the schedule module 410. The schedule module 410, visualization module 420, and automation module 430 may store, retrieve, adjust, and/or otherwise manipulate the contents of a schedule.

The various modules 410, 420, 430 may be communicatively coupled, wherein communicative coupling comprises any hardware and/or software system and/or method to transfer information from one module to another. Communicative coupling may comprise an electrical coupling, a shared and/or identifiable location in a memory (e.g. a system variable, information passed between software subroutines, a global variable in a software application, and the like), a wired or wireless network, and the like.

In one embodiment, the schedule module 410 may comprise any suitable system and/or method for outputting a schedule. As discussed above, a schedule may comprise various types of schedules such as a patient treatment schedule, a staff workflow schedule, a patient appointment schedule, and/or the like. The various types of schedules may be configured to display information specific for that type of schedule. For example, for clarity purposes, a patient schedule may include only the patient's name and their scheduled appointment time. In another example, the staff workflow schedule may include both the number of tasks a staff has to perform at any given time as well as provide information related to which patient is to receive the staff's attention and the timeframe in which they are set to receive it. In yet another example, the patient treatment schedule may include a list of requirement treatments for a given patient without being associated with any specific treatment times or staff member.

The schedule module 410 may retrieve the schedule from a physical storage (e.g., memory, hard drive, disk drive, optical disk, and the like) or non-physical storage (e.g., internet based storage and the like). The schedule module 410 may be configured to retrieve the schedule manually or automatically. For example, the interactive workflow scheduling system 200 may be configured to utilize the schedule module 410 to automatically load the schedule onto a computer system between the last shift of one day and the first shift of another day. The interactive workflow scheduling system 200 may be configured to manually load the schedule onto the computer system. For example, a staff member may log onto their machine at the start of their shift and manually request the schedule. In that instance, the schedule module 410 may be configured to receive the request from the staff member and retrieve the schedule requested by the staff member.

The schedule module 410 may also be configured to display or otherwise output the schedule. The schedule module 410 may be configured to display a patient and/or workforce schedule for a healthcare facility (e.g., a dialysis center). For example, in an embodiment, the schedule module 410 displays a text-based patient schedule, for example as shown in FIG. 3C. In a second exemplary embodiment, the schedule module 410 displays a workforce schedule, for example the schedule shown in FIG. 3A (for example displaying a shift schedule, information related to an employee, an option to edit the information (e.g. the pencil icon), and the like). The schedule module 410 may display statistics and/or other information related to the patient schedule and/or workforce schedule, for example as shown in FIG. 3B.

The schedule module 410 may further be configured to receive user input from any suitable input method provided and/or facilitated by a computing device. For example, the schedule module 410 may receive user inputs from a device such as a keyboard, phone, tablet, laptop, or the like. The schedule module 410 may be configured to receive the inputs manually or automatically. For example, a user may manually utilize the schedule module 410 to update, change, and/or otherwise adjust information regarding the schedule. Likewise, the schedule module 410 may be configured to automatically retrieve, modify, store, and update the schedule at a predetermined time, upon the occurrence of a specific condition, or at a predetermined interval. The schedule module 410 may change the schedule based on the user input, and may store the schedule to the memory.

The schedule module 410 may be communicatively coupled with the visualization module 420, and may transmit and/or receive the schedule to and/or from the visualization module 420. The schedule module 410 may also be communicatively coupled with the automation module 430, and may transmit and/or receive the schedule to and/or from the automation module 430. The visualization module 420 may be communicatively coupled with the automation module 430, and may transmit and/or receive the schedule to and/or from the automation module 430.

Still referring to FIG. 4, in one embodiment, the visualization module 420 may comprise any suitable system and/or method for visually representing the schedule for example by displaying the schedule as a line graph, Gantt chart, box graph, connected blocks, histogram, and the like. The visualization module 420 may be configured to visualize a patient appointment schedule, a staff workflow schedule, and/or any other schedule. For example, the visualization module 420 may be configured to retrieve the workflow schedule into a diagram comprising a number of patient block elements. Each of the patient blocks may be configured to correspond to a patient schedule. For example, one patient block may correspond to Patient X and a different patient block may correspond to Patient Y. A first patient block element may be configured to correspond to the start time for a task (e.g., the put-on time) and a second patient block element may be configured to correspond to the end time for a task (e.g., the take-off time).

In one embodiment, the visualization module 420 may be configured to apply different settings depending on what type of schedule is being displayed. For example, if the visualization module 420 is called upon to visually represent a patient schedule, then the visualization module 420 may be configured to only display the patient's name and the time block of their scheduled treatment for easier viewing purposes. If the visualization module 420 is called upon to visually represent a staff workflow graph for a particular staff member, the visualization module 420 may be configured to display a box graph of the workflow for that given staff member based on the time day so the staff member may easily reference what task they are scheduled to perform for a given time period.

In one embodiment, the visualization module 420 may be configured to display the visualized schedule as a connected blocks diagram graph. The visualization module 420 may receive the schedule from the schedule module 410. The visualization module 420 may retrieve the schedule from a physical storage device (e.g., a disk drive) and/or an internet-based storage device (e.g., cloud-based storage).

Now referring to FIGS. 4 and 5A, a connected blocks diagram 500 may help facilitate the visualization of a workflow schedule (e.g., patient schedule) that may be assigned to a staff member. Workflow may be defined as the amount of time and/or timing required by staff to perform certain tasks, and may be represented by a patient block 510. For example, workflow may comprise the time and/or timing for the tasks of putting-on and taking-off of patients in a medical facility. A "put-on" in a dialysis facility may comprise the process of connecting a patient to a dialysis machine, and a "take-off" may comprise the process of disconnecting the patient, for example removing and cleaning and/or disposing needles and tubing, waiting for the patient's site to stop bleeding, and cleaning the chair ("put-ons" as used in FIGS. 5A-C refers to both put-on and take-off events). Workflow may therefore represent the times that one or more staff persons are occupied (and/or unoccupied), and may represent how many staff persons are required by the facility for a particular time to perform all treatment tasks required at that time. The vertical axis in the connected blocks diagram 500 may represent the number of treatment tasks and/or the number of staff required, and the horizontal axis may represent the time at which those treatment tasks need to be performed and/or the duration of the treatment task that needs to be performed.

In one embodiment, the visualization module 420 may receive user input, and may change the workflow schedule and/or visual representation of the workflow schedule based on the user input. A user input may comprise any suitable method of system configured to modify, adjust, and/or otherwise affect a component of the workflow schedule in either the text-based format and/or the Connected Blocks diagram 500 (discussed below). For example, the user input may comprise a drag-and-drop motion, hovering over a patient block, clicking (single click and/or multiple clicks) one of the patient blocks, and the like. The visualization module 420 may be configured with any suitable method or system to prompt the user to confirm any adjustments to the patient block elements prior to saving and/or adjusting the workflow. For example, the user may be prompted by a pop-up message requesting whether they are sure they want to make the modifications.

In one embodiment, the visualization module 420 may be configured such that a user input may comprise an action causing one or more patient blocks in the connected blocks diagram to be adjusted. For example, if a "put-on" block is moved, its corresponding "take-off" block may be moved accordingly to maintain the same patient duration. The visual representation may thus be updated. The visualization module 420 may update the schedule accordingly, may store the schedule to the memory, and/or may transmit the change to the schedule to the schedule module 410 for processing. The visualization module 420 may comprise a suitable system or method for a user to confirm the changes to the schedule, for example a confirmation button, before the visualization module 420 will change the schedule or other related information.

Referring to FIGS. 5A-C, in one embodiment, the Connected Blocks diagram 500 displayed and operated by the visualization module 420 may be interactive and may allow the user to adjust or otherwise manipulate the components of the connected blocks diagram 500 to alter the schedule. The Connected Blocks 500 diagram may comprise patient blocks 510 that represent time required by a staff person, for example for patient put-on or take-off. In the context of a dialysis center, when a patient arrives for their appointment, they are put-on (hooked up) to their dialysis machine by a staff member. After treatment is completed, the staff member will perform a take-off procedure, which may involve taking off all the needles and tubing, cleaning and injection site, and cleaning the chair and/or machine.

In one embodiment, the patient blocks 510 may be configured to store and/or display information related to the patient, their appointment, their treatment, the staff member assigned to them, and the like. For example, when viewing the Connected Blocks diagram 500, a user may hover over a patient block with the mouse cursor. In this manner, information about the patient (their name, date of birth, address) may be displayed. What information is displayed by the patient block may be dynamically changed according to system constraints and/or user preferences. For instance, the patient block 510 may be configured to only present basic information by default, and each individual dialysis treatment center may customize what is displayed according to their own preferences.

Now referring to FIG. 5B, in one embodiment, a patient block for a patient put-on 520 may be linked, and/or otherwise associated with, a patient block for take-off 530 for the same patient, and the time between the two patient blocks may represent the treatment time for the patient. For example, put-on 520 occurs at 0430 hours and the corresponding take-off 530 occurs at 0930 hours. The Connected Blocks diagram 500 may be configured with any suitable system or method to visually indicate which specific put-on 520 corresponds to which specific take-off 530. For example, the Connected Blocks diagram may be configured such that when a staff member hovers a mouse icon over the put-on 520 block, a line is drawn connecting that put-on 520 block with its corresponding take-off 530 block. The Connected Blocks diagram 500 may be configured to utilize any system or method to indicate corresponding put-on 520 and take-off 530 blocks. For example, the Connect Blocks diagram 500 may be configured to highlight the corresponding block when one of the put-on 520 or take-off 530 block is highlighted. The Connected Blocks diagram 500 may be configured to display additional information upon the occurrence of an event. For example, hovering a mouse cursor, single-clicking, double-clicking, drag-and-drop actions performed on the put-on 520 and take-off 530 blocks may be configured to produce different results and/or display different information. These different results may comprise displaying additional information, manipulating information, and/or updating either one of or both the text-based and/or the visualized schedule.

In one embodiment, the Connected Blocks diagram 500 may be configured to link and/or otherwise associate additional information related to the patient, the appointment, the staff, and/or the like to the put-on 520 and/or take-off 530 blocks. For example, the Connected Blocks diagram 500 may be configured such that when a mouse cursor is hovered over one of the put-on 520 or take-off 530 blocks, information regarding the patient (name, date of birth, address, etc.) is displayed, as well as their scheduled appointment time, and special instructions and/or requests, and the like. Displaying information in this manner may alleviate the requirement of referencing additional materials other than the Connected Blocks diagram 500.

Referring to FIGS. 4 and 5C, the patient blocks 510 may be implemented in a drag-n-drop manner. For example, the user moving one of the patient blocks 510 (540 or 550) may cause the other patient block 510 for the same patient (540 or 550) to move accordingly to maintain the same treatment time and/or another other restrictions/requirements. The patient blocks 510 may be linked to the workflow schedule so that the workflow schedule may be altered according to the alterations to (or to otherwise match) the schedule shown by the Connected Blocks diagram 500.

In one embodiment, the Connected Blocks diagram 500 may be configured to interact with the schedule module 410, the visualization module 420, and/or the automation module 430. For example, when a staff member manipulates the patient blocks 540 or 550, the new information may be sent to the schedule module 410. In another example, if the patient blocks 540 or 550 are modified, the visualization module 420 may be utilized to provide a new visual schedule that includes the latest up to date information. In yet another example, the automation module 430 (discussed below) may be utilized to verify whether certain constraints, restrictions, and/or requirements are satisfied by the latest modifications to the patient blocks 540 or 550.

In one embodiment, the automation module 430 may comprise any suitable system or method for improving and/or optimizing the workflow of a schedule. The automation module 430 may create a new schedule and/or update an existing schedule to achieve the improvement and/or optimization of the workflow. The schedule may, for example, be received from the schedule module 410 or visualization module 420, and the automation module 430 may store and/or transmit the new or updated schedule to the schedule module 410 and/or visualization module 420. The automation module 430 may be configured to take into account any number of constraints, restrictions, and/or requirements when improving and/or optimizing the workflow of a schedule.

In one embodiment, improving and/or optimizing the workflow may be determined according to any suitable criteria, such as: reducing and/or minimizing the amount of overtime required by staff, reducing and/or minimizing the number of technicians required to cover a patient schedule, and the like. The improvement and/or optimization may be implemented by solving (for example using an Xpress solver) a model comprising an objective function subject to certain constraints as outlined below. In one embodiment, the model may be coded in the GNU Mathematical Programming Language environment.

In one embodiment, the automation module 430 may be utilized to reduce overtime hours for staff member. The automation module may utilize any suitable system, method, and/or algorithm to optimize the schedule. For example, in one embodiment, the following optimization model may be utilized by the automation module 430 to reduce overtime hours.

For example, given the following sets of entities:
I set of chairs, indexed i=1, . . . , m
J set of patients, indexed j=1, . . . , n
T set of time periods, indexed t=a, . . . , υ
T' set of time periods, indexed τ=a, . . . , υ
And the following parameters:
$d_j$ duration of dialysis treatment for patient j
$s_j$ start of time window for on time of patient j
$e_j$ end of time window for on time of patient j
$p_j$ put-on time duration of patient j
$o_j$ take-off time duration of patient j
m number of dialysis chairs in clinic
n number of patients in clinic
a clinic opening time
υ clinic closing time y idle time for chair
$r_j$ total treatment time
$a_{j\tau t}$ identifies conflicting periods of $p_j$ and $o_j$ for patient j $$r_j = p_j - 1 + d_j + o_j + y$$

$a_{j\tau t}=1$ if $\tau \leq t$ and $\tau + p_j \geq t$ or if $t \geq \tau + p_j + d_j$ and $t \leq \tau + p_j + d_j + o_j$ $a_{j\tau t}=0$ otherwise And the following decision variables:
$x_{ijt}=1$ if put on process of patient j at chair i starts at time t; otherwise=0
w=0 if schedule is feasible without conflicting $p_j$ and $o_j$; otherwise=1

A number of constraints may be utilized by the automation module 430, these constraints may be configured to ensure that the optimization algorithm does not violate any requirements put in place by the treatment center. For example, a constraint may be implemented to allow at most one patient to be scheduled at any time on any available chair:

$$\sum_{i \in I} \sum_{h=max(a,t-(p_j+d_j+o_j+y-1))}^{v} x_{ijh} \leq 1 \ \forall \ i \in I, t \in T$$

A different constraint may be implemented such that each patient starts their dialysis on only one chair at only one point in time.

$$\sum_{i \in I} \sum_{t \in T} x_{ijt} = 1 \ \forall \ j \in J$$

Another constraint may be configured to block a patient from being scheduled before the start of the patient's put-on window.

$$\sum_{i \in I} \sum_{t=a}^{s_j-1} x_{ijt} = 0 \ \forall \ j \in J$$

Yet another constraint may be configured to block a patient from being scheduled after the end of the patient put-on window.

$$\sum_{i \in I} \sum_{t=min(e_j+1, v-r_j)}^{v} x_{ijt} = 0 \ \forall \ j \in J$$

Yet another constraint may be configured to prevent a patient being put on or taken off during another patient's put on or take off process. In one embodiment, this constraint is configured to allow at most two puton and takeoff procedures to occur at simultaneously.

$$\sum_{i} \sum_{j} \sum_{t} a_{j\tau i} x_{ij\tau} \leq 1 + w \ \forall \ t \in T$$

In one embodiment, the objective of the optimization model above may be configured to minimize the binary variable w. If the value of w is zero (0), then that may indicate that the schedule does not contain any overtimes for its staff. If the value of w is one (1), then that may indicates at least one overlap between one patient's puton and takeoff procedure and another patient's puton and takeoff procedure.

In another embodiment, the automation module 430 may be utilized to performing general purpose optimization tasks other than reducing overtime hours for staff members. The automation module may utilize any suitable system, method, and/or algorithm to optimize the schedule. For example, in one embodiment, the following optimization model may be utilized by the automation module 430 in a general optimization approach.

Given the following assumptions:
Assumptions and notation:
1. Time is given in increments of 5 (minutes)
2. Schedule produces single day
And the following sets:
Sets:
I set of chairs, indexed i=1, . . . , m
J set of patients, indexed j=1, . . . , n
T set of time periods, indexed t=a, . . . , $v$
And the following parameters:
Parameters:
$d_j$ duration of dialysis treatment for patient j
$s_j$ start of time window for on time of patient j
$e_j$ end of time window for on time of patient j
$p_j$ put on time duration of patient j
$o_j$ take off time duration of patient j
m number of dialysis chairs in clinic
n number of patients in clinic
a clinic opening time
$v$ clinic closing time
y idle time for chair (typically 15 or 20 minutes)
And the following decision variables:
Decision Variables:
$x_{ijt}=1$ if put on process of patient j at chair i starts at time t; otherwise, =0
$z_{it}=1$ if technician is needed for chair i at time r; otherwise, =0
0 integer representing the number of technicians needed to cover a patient schedule A number of constraints may be utilized by the automation module 430 while performing general optimization tasks, these constraints may be configured to ensure that the optimization algorithm does not violate any requirements put in place by the treatment center. For example, a constraint may be implemented that states each patient j will only be scheduled on one chair i at one timeslot t:

$$\sum_{i \in I} \sum_{t=N_i}^{t=min(c,v-(p_t+d_t+o_t+y-1))} x_{ijt} = 1 \ \forall \ j \in J$$

Another constraint may be configured to permit at most one patient to be scheduled at any time on any chair:

$$\sum_{j \in J} \sum_{h=max(a,t-(p_t+d_t+o_t+y-1))}^{t} x_{ijh} \leq 1 \ \forall \ i \in I, t \in T$$

Yet another constraint may be configured to not allow a patient to be scheduled until their put-on time window opens at time $s_j$:

$$\sum_{i \in I} \sum_{t=a}^{s_j-1} x_{ijt} = 0 \ \forall \ j \in J$$

Yet another constraint may be configured to not allow a patient to be scheduled after their put-on time window closes at time $e_j$:

$$\sum_{i \in I} \sum_{t=c}^{v} x_{ijt} = 0 \ \forall \ j \in J$$

Yet another constraint may be configured to determine how many staff members may be needed at each chair at each time slot:

| (Put on) | (Take off) |
|---|---|
| $Z_{i,t+(p,-1)} \geq x_{ijt}$ | $Z_{i,t+p_s-1+d_s+(o,-1)} \geq x_{ijt}$ |
| $Z_{i,t+(p,-2)} \geq x_{ijt}$ | $Z_{i,t+p_s-1+d_s+(o,-2)} \geq x_{ijt}$ |
| $\vdots$ | $\vdots$ |
| $Z_{i,t+(p)} \geq x_{ijt}$ | $Z_{i,t+p_s-1+d_s+(o,-o_s)} \geq x_{ijt}$ |

$\forall \ i \in I, j \in J, t \in T$

In one embodiment, the objective is to minimize the value of $\theta$ (subject to the various constraints), wherein:

$$\theta \geq \sum_{i \in I} z_{it} \ \forall \ t \in T$$

In one embodiment, a basic schedule to be manipulated by the automation module 430 to improve and/or optimize the workflow may comprise the assignment of patients to shifts. For example, the basic schedule may comprise information about which patients are scheduled to be on the first, second, and third shifts of the clinic, and using that information, each first-shift patient can be set to have an on-time of 6:00 AM (or whatever the starting time of the clinic is), each second-shift patient can be set to have an on-time of 9:00 AM, and likewise for the third-shift patients. The automation module 430 may then use this as the starting point for improving and/or optimizing the workflow of the schedule. More than one optimal solution may exist, and the automation module 430 may stop at the first solution it finds that meets all criteria or the solution that meets the highest number of criteria. Further constraints may be set (for example re-gauging initial on-times) and the automation module 430 may be rerun to obtain new results.

The particular implementations shown and described are illustrative of the invention and its best mode and are not intended to otherwise limit the scope of the present technology in any way. Indeed, for the sake of brevity, conventional manufacturing, connection, preparation, and other functional aspects of the system may not be described in detail. Furthermore, the connecting lines shown in the various figures are intended to represent exemplary functional relationships and/or steps between the various elements. Many alternative or additional functional relationships or physical connections may be present in a practical system.

In the foregoing description, the present technology has been described with reference to specific exemplary embodiments. Various modifications and changes may be made, however, without departing from the scope of the present technology as set forth. The description and figures are to be regarded in an illustrative manner, rather than a restrictive one and all such modifications are intended to be included within the scope of the present technology. Accordingly, the scope of the present technology should be determined by the generic embodiments described and their legal equivalents rather than by merely the specific examples described above. For example, the steps recited in any method or process embodiment may be executed in any appropriate order and are not limited to the explicit order presented in the specific examples. Additionally, the components and/or elements recited in any system embodiment may be combined in a variety of permutations to produce substantially the same result as the present technology and are accordingly not limited to the specific configuration recited in the specific examples.

Benefits, other advantages and solutions to problems have been described above with regard to particular embodiments. Any benefit, advantage, solution to problems or any element that may cause any particular benefit, advantage or solution to occur or to become more pronounced, however, is not to be construed as a critical, required or essential feature or component.

The terms "comprise", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

The invention claimed is:

1. A network-enabled workflow management system for a dialysis center accessible by a user device, comprising:
a memory communicatively coupled to the network-enabled workflow management system for storing a plurality of patient schedules;
a schedule module communicatively linked to the memory and the user device, wherein the schedule module is configured to retrieve, via the network, the plurality of patient schedules from the memory; and
a visualization module communicatively linked to the schedule module and the user device, wherein the visualization module is configured to:
retrieve, via the network, the plurality of patient schedules from the memory;
convert the retrieved plurality of patient schedules into a workflow schedule diagram, wherein for each individual patient schedule from the plurality of patient schedules the visualization modules generates:
a first patient block element corresponding to a put-on procedure comprising an amount of staff time for a start task required before a beginning of a dialysis treatment time; and a second patient block element corresponding to a take-off procedure comprising a second amount of staff time for an end task required at an end of the dialysis treatment time;

display only the generated first and second patient block elements for the plurality of patient schedules as the workflow schedule diagram to the user device in a visual based format, wherein:

all first and second patient block elements are arranged along a single horizontal time axis; and any first or second patient block elements of a first individual patient schedule occurring at a same time along the horizontal time axis as the first or second patient block elements of a second individual patient schedule are stacked on top of each other along a vertical occurrence axis to identify an overlap occurrence greater than one for that same time;

selectively adjust the workflow schedule diagram to remove any stacked first and second patient block elements according to received user inputs corresponding to:

a user selected first or second patient block element from either the first or second individual patient schedule having an overlap at the same time; and moving the selected first or second patient block to an alternative time slot along the horizontal time axis to remove the overlap occurrence between the selected first or second patient block element and the unselected first or second patient block element of the other patient;

adjust the unselected first or second patient block element to a second time slot along the horizontal time axis to maintain the dialysis treatment time corresponding to each individual patient schedule;

update the plurality of patient schedules according to the adjusted workflow schedule diagram;

save the plurality of patient schedules in the memory according to any user adjustments; and update the displayed workflow schedule diagram on the user device according to the adjusted workflow schedule diagram.

2. A network-enabled workflow management system for a dialysis center according to claim 1, wherein the schedule module is configured to display the retrieved workflow schedule to a user in a text based format.

3. A network-enabled workflow management system for a dialysis center according to claim 1, wherein the visualization module is configured to prompt the user to confirm any adjustments to the patient block elements prior to saving the adjusted workflow.

4. A network-enabled workflow management system for a dialysis center according to claim 1, wherein the visualization module is configured to display a line representing the treatment time between a first patient block element and a second patient block element when one of the first and second block elements is selected by the user.

5. A network-enabled workflow management system for a dialysis center according to claim 1, wherein the plurality of patient block elements is configured to display information related to the patient.

6. A network-enabled workflow management system for a dialysis center according to claim 1, wherein the visual based format of the workflow schedule is a connected blocks diagram.

7. An internet-based workflow management system for a dialysis center accessible by a user device connected to the internet via a network, comprising:

an internet-based storage medium communicatively coupled to the user device, wherein the internet-based storage medium is configured to:

operate the internet-based workflow management system; and store, in the internet-based storage medium, a plurality of patient schedules;

a schedule module communicatively linked to the internet-based storage medium and the user device, wherein the schedule module is configured to retrieve, via the network, the plurality of patient schedules; and a visualization module communicatively linked to the schedule module and the user device, wherein the visualization module is configured to:

retrieve, via the network, the plurality of patient schedules from the internet-based storage medium;

convert the retrieved plurality of patient schedules into a workflow schedule diagram, wherein for each individual patient schedule from the plurality of patient schedules the visualization modules generates:

a first patient block element corresponding to a put-on procedure comprising an amount of staff time for a start task required before a beginning of a dialysis treatment time; and a second patient block element corresponding to a take-off procedure comprising a second amount of staff time for an end task required at an end of the dialysis treatment time;

display only the generated first and second patient block elements for the plurality of patient schedules as the workflow schedule diagram to the user device in a visual based format, wherein:

all first and second patient block elements are arranged along a single horizontal time axis; and any first or second patient block elements of a first individual patient schedule occurring at a same time along the horizontal time axis as the first or second patient block elements of a second individual patient schedule are stacked on top of each other along a vertical occurrence axis to identify an overlap occurrence greater than one for that same time;

selectively adjust the workflow schedule diagram to remove any stacked first and second patient block elements according to received user inputs corresponding to:

user selected first or second patient block element from either the first or second individual patient schedule having an overlap at the same time; and moving the selected first or second patient block to an alternative time slot along the horizontal time axis to remove the overlap occurrence between the selected first or second patient block element and the unselected first or second patient block element of the other patient;

adjust the unselected first or second patient block element to a second time slot along the horizontal time axis to maintain the dialysis treatment time corresponding to each individual patient schedule;

update the plurality of patient schedules according to the adjusted workflow schedule diagram;

save the plurality of patient schedules in the internet-based storage medium according to any user adjustments; and update the displayed internet-based format and the workflow schedule diagram on the user device according to the adjusted workflow schedule diagram.

8. An internet-based workflow management system for a dialysis center according to claim 7, wherein the schedule module is configured to display the retrieved workflow schedule to a user in a text-based format.

9. An internet-based workflow management system for a dialysis center according to claim 7, wherein the visualization module is configured to prompt the user to confirm any adjustments to the patient block elements prior to saving the adjusted workflow.

10. An internet-based workflow management system for a dialysis center according to claim 7, wherein the visualization module is configured to display a line representing the treatment time between a first patient block element and a second patient block element when one of the first and second block elements is selected by the user.

11. An internet-based workflow management system for a dialysis center according to claim 7, wherein the plurality of patient block elements is configured to display information related to the patient.

12. An internet-based workflow management system for a dialysis center according to claim 7, wherein the visual based format of the workflow schedule is a connected blocks diagram.

13. A cloud-based method for visual workflow management for a plurality of patient schedules hosted on a cloud-based server implemented by a computer having a display device and operated by a user, comprising:

using a visualization module to:

retrieve the plurality of patient schedules from the cloud-based server;

convert the retrieved plurality of patient schedules into a workflow schedule diagram, wherein for each individual patient schedule from the plurality of patient schedules the visualization modules generates:

a first patient block element corresponding to an amount of staff time required for a start task performed before a beginning of a treatment time; and a second patient block element corresponding to a second amount of staff time required for an end task performed at an end of the treatment time; and display only the generated first and second patient block elements for the plurality of patient schedules as the workflow schedule diagram to the display device in a visual based format, wherein:

all first and second patient block elements are arranged along a single horizontal time axis; and any first or second patient block elements of a first individual patient schedule occurring at a same time along the horizontal time axis as the first or second patient block elements of a second individual patient schedule are stacked on top of each other along a vertical occurrence axis to identify an overlap occurrence greater than one for that same time;

selectively adjusting the workflow schedule diagram to remove any stacked first and second patient block elements according to received user inputs corresponding to:

a user selected first or second patient block element from either the first or second individual patient schedule having an overlap at the same time; and moving the selected first or second patient block to an alternative time slot along the horizontal time axis to remove the overlap occurrence between the selected first or second patient block element and the unselected first or second patient block element of the other patient;

adjusting the unselected first or second patient block element of the selected patient to a second time slot along the horizontal time axis to maintain the treatment time corresponding to each individual patient schedule;

updating the plurality of patient schedules according to the adjusted workflow schedule diagram;

saving the plurality of patient schedules in the memory according to any user adjustments; and updating the displayed workflow schedule diagram on the display device according to the adjusted workflow schedule diagram.

14. A cloud-based method for visual workflow management according to claim 13, wherein the visualization module is configured to display a line representing the treatment time between a first patient block element and a second patient block element when one of the first and second block elements is selected by the user.

15. A cloud-based method for visual workflow management according to claim 13, wherein the plurality of patient block elements is configured to display information related to the patient.

16. A cloud-based method for visual workflow management according to claim 13, wherein a modification to the visualized schedule is reflected in a text-based format schedule.

17. A cloud-based method for visual workflow management according to claim 13, wherein the visual based format of the workflow schedule comprises a connected blocks diagram.

18. A cloud-based method for visual workflow management according to claim 13, wherein an automation module is configured to optimize the workflow schedule.

* * * * *